(12) United States Patent
Miller

(10) Patent No.: US 8,407,011 B2
(45) Date of Patent: Mar. 26, 2013

(54) MOBILE SAMPLING OF TARGET SUBSTANCES

(75) Inventor: Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 588 days.

(21) Appl. No.: 12/534,393

(22) Filed: Aug. 3, 2009

(65) Prior Publication Data

US 2011/0029253 A1 Feb. 3, 2011

(51) Int. Cl.
*G01N 33/48* (2006.01)
(52) U.S. Cl. .......................................................... 702/19
(58) Field of Classification Search ...................... 702/19
See application file for complete search history.

(56) References Cited

U.S. PATENT DOCUMENTS

| | | | |
|---|---|---|---|
| RE30,627 E * | 5/1981 | Bagshawe et al. .............. | 436/48 |
| 2006/0014300 A1 | 1/2006 | Maurer et al. | |

FOREIGN PATENT DOCUMENTS

| | | |
|---|---|---|
| WO | 2004059441 A2 | 7/2004 |
| WO | 2008086507 A1 | 7/2008 |

OTHER PUBLICATIONS

Kim, et al., A reconfigurable computing platform for plume tracking with mobile sensor networks, Unmanned Systems Technology VIII, Proceedings of SPIE, pp. 623011-1-623011-11, 2006.
Marques et al., Environmental monitoring with mobile robots, 2005 International Conference on Intelligent Robots and Systems, IEEE, pp. 3624-3629, 2005.
Cui et al, A swarm-based fuzzy logic control mobile sensor network for hazardous contaminants localization, 2004 IEEE International Conference on Mobile Ad-hoc and Sensor Systems, IEEE, pp. 194-203, 2005.
International Search Report and Written Opinion for International Application No. PCT/US2010/038335 mailed on Aug. 16, 2010.
Zoltan Takats, et al, Mass Spectrometry Sampling Under Ambient Conditions with Desorption Electrospray Ionization, Science, Oct. 15, 2004, pp. 471-473, vol. 306, USA.
Demian R. Ifa, Nicholas E. Manicke, Allison L. Dill, R. Grahm Cooks, Latent Fingerprint Chemical Imaging by Mass Spectrometry, Science, Aug. 8, 2008, pp. 805, vol. 321, USA.
Desorption Electrospray Ionization, Wikipedia, the Free Encyclopedia, http://en.wikipedia.org/wiki/Desorption_electrospray_ionization, accessed Jul. 16, 2009.

* cited by examiner

*Primary Examiner* — Jerry Lin

(57) ABSTRACT

Implementations for sampling one or more target substances using a mobile device configured to sample multiple substances at various locations, analyze the substances and map the substances to the sampling locations are generally disclosed.

9 Claims, 6 Drawing Sheets

600 A computer program product.

602 A signal bearing medium.

604 Machine-readable instructions, which, if executed by one or more processors, operatively enable a computing device to:

receive one or more target substances from a first physical location via a first portion of a sample substrate;

correlate the first physical location with the first portion of the sample substrate;

receive one or more target substances from a second physical location via a second portion of the sample substrate;

correlate the second physical location with the second portion of the sample substrate; and/or associate a chemical analysis result of the first portion of the sample substrate and a chemical analysis result of the second portion of the sample substrate with a geometric map based at least in part on the correlation of the first physical location and the second physical location with the first portion of the sample substrate and the second portion of the sample substrate respectively.

| 606 a computer-readable medium. | 608 a recordable medium. | 610 a communications medium. |

FIG. 6

MOBILE SAMPLING OF TARGET SUBSTANCES

BACKGROUND

The senses of taste and smell are at their heart recognition of volatile molecules. The sense of smell is designed to provide an animal with the ability to identify potentially helpful or harmful molecules. In animals, this sense occurs by the activation of thousands of individual chemical receptors, which give a qualitative and analog output. This qualitative information is of high enough quality to keep animals mostly healthy. Taste and smell phenomena may be used outside their normal relationship to food and health, for example in the use of bomb-sniffing dogs.

Man made scent-based detection methods may examine high volatility compounds by sampling air in an area of interest. For example, analogs of biological 'smell', such as a polymer-based biomimetic smelling (e.g. electronic noses developed by the company Cyrano), have been developed for qualitative analysis.

Another technique of molecular detection may use mass spectroscopy, which may identify molecules by their exact molecular weight. Unlike biomimetic smelling, mass spectroscopy may identify and quantify similar molecules in a complex mixture, such as by detailing the components of gasoline or the decomposition products from foodstuff.

In some types of gas analysis techniques, a canister may be placed under vacuum and sealed, then brought to an area for gas sampling. A valve on the canister may be opened slightly, and volatile gases from this area may be admitted to the canister. After a set time (which may be up to days), the canister valve may be closed, and the canister and its contents may be brought to a mass spectrometer for analysis.

In other techniques, a surface may be analyzed by mass spectroscopy by directly bombarding such a surface with laser energy while the surface is in a vacuum. Such techniques may identify molecules not generally considered as volatile. However, operation entirely in a vacuum may have drawbacks.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 6 illustrates an example computer program product; and

DETAILED DESCRIPTION

Figure 1:
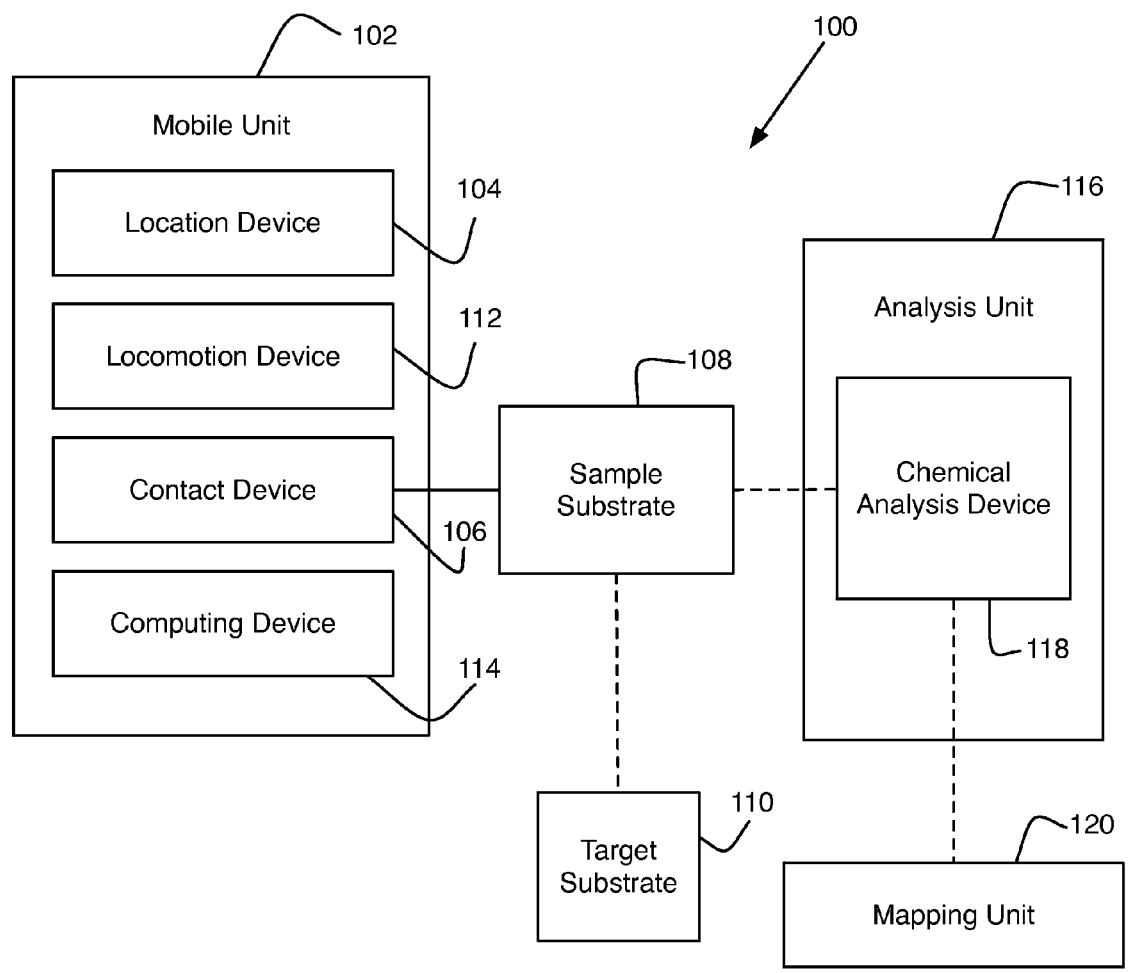
FIG. 1 illustrates a diagram of an example system that may be arranged to sample one or more target substances.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, systems and/or computer program products related to mobile sampling of one or more target substances.

Scent-based detection may examine high volatility compounds by sampling air in an area of interest. Such high volatility compounds may be adsorbed to surfaces as well. One or more examples discussed below may take advantage of such adsorption to transfer target substances, including low volatility compounds and/or high volatility compounds, to an intermediate sample substrate from a target substrate for chemical analysis. Additionally or alternatively, information regarding the physical location associated with individual sampling transfers of target substances to a sample substrate may be gathered. In such a case, two or more samples of target substances transferred to a sample substrate may be associated with the corresponding physical locations and associated with the corresponding chemical analysis results. For example, such corresponding chemical analysis results may be associated with such corresponding physical locations via a geometric map.

FIG. 1 illustrates an example system 100 that may be arranged to sample one or more target substances, in accordance with at least some embodiments of the present disclosure. In the illustrated example, system 100 may include a mobile unit 102. Mobile unit 102 may be adapted for mobile sampling of target substances. Mobile unit 102 may include a location device 104. Location device 104 may be adapted to determine a physical location of the mobile unit 102. For example, location device 104 may determine locations via global positioning system (GPS), triangulation from emissive sources (e.g. cell networks), one or more sensors (e.g. proximity sensor or rangefinder), an internal mechanism (e.g. setting a zero location and measuring other locations with respect to the established zero location), a visual system adapted to locate and track the mobile unit 102, the like, and/or combinations thereof.

Mobile unit 102 may include a contact device 106. Contact device 106 may be adapted to contact a portion of a sample substrate 108 to one or more target substances associated with a target substrate 110. For example, contact device 106 may include one or more hydraulic devices, cams, rotational motors, linear actuators, biasing devices, the like, and/or combinations thereof configured to removably contact sample substrate 108 to target substrate 110. In some cases, target substrate 110 may be a unitary substrate; alternatively, target substrate 110 may be a plurality of contiguous or non-contiguous substrates.

Mobile unit 102 may include a locomotion device 112. Locomotion device 112 may be adapted to move the mobile unit 102 between two or more physical locations with respect to the target substrate 112. For example, locomotion device 112 may include one or more wheels, tracks, hydraulic devices, cams, rotational motors, linear actuators, biasing devices, the like, and/or combinations thereof configured to move the mobile unit 102 between two or more physical locations.

Mobile unit 102 may include a computing device 114. Computing device 114 may be operatively associated with the location device 104, the contact device 106, and/or the locomotion device 112 and adapted to control their operation or exchange information. For example, computing device 114 may be adapted to correlate a given physical location, as determined via location device 104, with an associated portion of the sample substrate 108 utilized in a given sampling of target substrate 110.

An analysis unit 116 may be operatively associated with sample substrate 108. Analysis unit 116 may include a chemical analysis device 118 that may be adapted to perform a chemical analysis of one or more portions of the sample substrate 108. For example, chemical analysis device 118 may return a chemical analysis result associated with target substances transferred from a target substrate 110 to sample substrate 108.

Chemical analysis device 118 may include a mass spectrometer. One such chemical analysis device 118 may employ a mass spectroscopy technique called desorption electrospray ionization (DESI). In such an example, a DESI-type chemical analysis device may spray ionized water onto the sample surface 108. The target substances on the sample surface 108 may be ionized and ejected from the sample surface 108. These ionized and ejected target substances may then be admitted to an inlet of a mass spectrometer for chemical analysis. In such an example, a DESI-type chemical analysis device 118 may permit the target substances associated with the sample surface 108 to be extracted for examination without the need to be admitted into a vacuum before analysis. A DESI-type chemical analysis device 118 may also permit a sample surface 108 to be scanned with high spatial resolution, such as with a resolution of around 150 microns, for example.

In other examples, chemical analysis device 118 may employ a Fourier transform spectroscopy (FT-IR) or Raman spectroscopy. Such FT-IR and/or Raman spectroscopies may operate with an incident beam focused through a microscope (not shown) to achieve increased spatial resolution. In examples utilizing FT-IR and/or Raman spectroscopies, sample substrate 108 may be reflective. For example, sample substrate 108 may include a metalized polymer or the like.

In some examples, the mobile unit 102 may be free to move separate and apart from analysis unit 116. In such an example, the mobile unit 102 may not be operably coupled to the analysis unit 114 or adapted to move the analysis unit 114 from location to location. In such a case, the mobile unit 102 may be adapted to gather target substances onto the sample substrate 108 and bring the sample substrate 108 to the analysis unit 114 for chemical analysis.

In other examples, the mobile unit 102 (e.g. the locomotion device 112) may be operably coupled to the analysis unit 116 and adapted to move the analysis unit 116 between physical locations. In such a case, the mobile unit 102 may move the analysis unit 114 from location to location so that the analysis unit 114 may perform a chemical analysis at the end of gathering target substances onto a sample substrate 108. Alternatively, the mobile unit 102 may move the analysis unit 114 from location to location so that the analysis unit 114 may perform a chemical analysis at designated intervals. Additionally or alternatively, the mobile unit 102 and the analysis unit 116 may optionally share computing device 114.

A mapping unit 120 may be operatively associated with analysis unit 116 and/or mobile unit 102. Mapping unit 120 may be operatively associated in communication with the analysis unit 116 or mobile unit 102 to exchange information. For example, mapping unit 120 may be adapted to associate chemical analysis results from analysis unit 116 associated with two or more portions of the sample substrate 108 with a geometric map of two or more physical location where target substances were sampled via mobile unit 102.

In some examples, the mobile unit 102 (e.g. the locomotion device 112) may be operably coupled to the mapping unit 120 and adapted to move the mapping unit 120 between physical locations. In such a case, the mobile unit 102 and the mapping unit 120 may optionally share computing device 114. Similarly, in further examples, the mobile unit 102 (e.g. the locomotion device 112) may be operably coupled to the analysis unit 116 and the mapping unit 120 and adapted to move the analysis unit 116 and the mapping unit 120 between physical locations. In such a case, the mobile unit 102, the analysis unit 116, and/or the mapping unit 120 may optionally share one or more computing devices 114.

Figure 2:
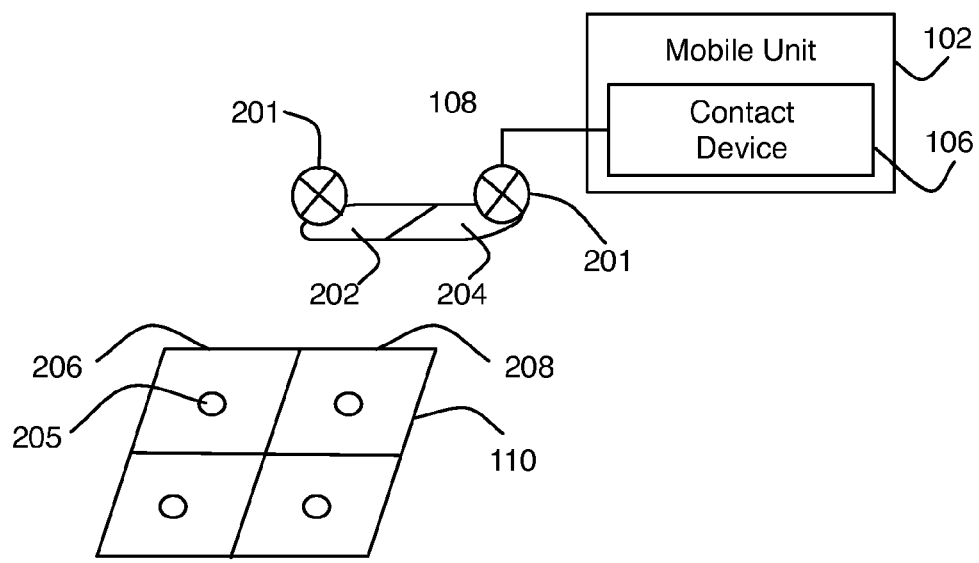
FIG. 2 illustrates a diagram of an example mobile unit.

FIG. 2 illustrates an example mobile unit arranged in accordance with at least some embodiments of the present disclosure. In the illustrated example, the contact device 106 of the mobile unit 102 may be operably coupled to the sample substrate 108. The illustrated sample substrate 108 may include a flexible tape and adhesive associated with the flexible tape. For example, a flexible tape-type sample substrate 108 may be operably coupled to one or more spools 201 adapted to rotatably hold the sample substrate 108.

The illustrated sample substrate 108 may include two or more portions, such as first portion 202 and second portion 204. In some examples, the first portion 202 of sample substrate 108 may be contacted to one or more target substances 205 from a first physical location 206. Similarly, the second portion 204 of sample substrate 108 may be contacted to one or more target substances 205 from a second physical location 208 of target substrate 110. For example, sample substrate 108 may be contacted to one or more target substances 205 from the first physical location 206 and continuously or semi-continuously rolled across target substrate 110 via spools 201.

In other examples, the first portion 202 of sample substrate 108 may be contacted to one or more target substances 205 associated with the first physical location 206, removed, advanced via one or more spools 201 to the second portion 204 of sample substrate 108, and the second portion 204 of sample substrate 108 may be contacted to one or more target substances 205 associated with the second physical location 208. In such a case, such one or more spools 201 may be operably coupled to one or more hydraulic devices, cams, rotational motors, biasing devices, the like, and/or combinations thereof adapted to rotate sample substrate 108 via spools 201. Such spools 201 may be included in or be separate from contact device 106.

In some examples, the one or more spools 201 may be adapted to roll up sample substrate 108 as target substances 205 are collected. In some cases, such target substances 205 may be sufficiently volatile to move across the target substrate 110 or sample substrate 108 during sample collection. By rolling the sample substrate 108 up as the target substances 205 are collected, it may be possible to contain volatile target substances 205 and reduce or prevent cross-contamination across the target substrate 110 or sample substrate 108.

In operation, location data may be collected by location device 104 (see FIG. 1) so that the locations of the mobile unit 102 may be correlated with specific positions of the sample substrate 108. For example, location data may be collected to correlate locations of the mobile unit 102 with specific positions of the sample substrate 108 with respect to the spools 201.

In general, the sample substrate 108 may be a flexible planar surface, a flexible tape, the like, and/or combinations thereof. The number of components or type of components making up the sample substrate 108 may be selected so as to limit the impact on chemical analysis. For example, in some applications the type of plasticizers and/or the number of plasticizer components of the sample substrate 108 may be selected so as to avoid creating a signal in a chemical analysis that might obscure a target substance 205. In examples utilizing a flexible tape, the sample substrate 108 may be composed of a thin metal, flexible polymer material (e.g. polyethylene terephthalate $(C_{10}H_8O_4)_n$ (PET) or other polyesters), or the like. In examples utilizing FT-IR and/or Raman spectroscopies, sample substrate 108 may be reflective. For example, sample substrate 108 may include a metalized polymer, such as a metalized PET (e.g. Mylar) or the like.

Additionally or alternatively, the sample substrate 108 may include an adhesive adapted to transfer a target substance 205 from a target surface to a sample substrate 108. As discussed above, the number and/or type of components making up the sample substrate 108 may be selected so as to limit the impact on chemical analysis. In some applications the type of adhesives and/or the number of adhesives of the sample substrate 108 may be selected so as to avoid creating a signal in a chemical analysis that might obscure a target substance 205. For example, the sample substrate 108 may include an adhesive having simple repeat units, such as polyethylene glycol $(C_{2n+2}H_{4n+6}O_{n+2})$ or the like. In another example, the sample substrate 108 may include an adhesive composed of polymers containing poly(ethyl vinyl ether). Such a poly(ethyl vinyl ether) polymer may have simple repeat units of $C_4H_8O$.

Figure 3:
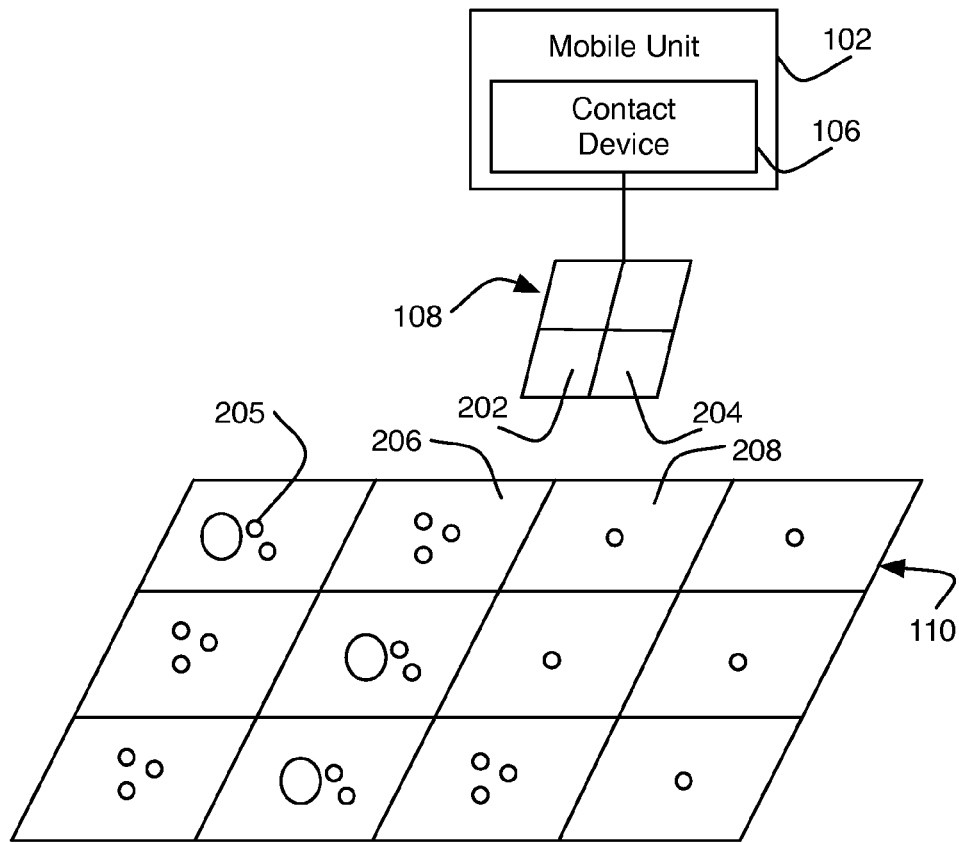
FIG. 3 illustrates a diagram of an example mobile unit in operation.

FIG. 3 illustrates an example mobile unit in operation, arranged in accordance with at least some embodiments of the present disclosure. In the illustrated example, the contact device 106 of the mobile unit 102 may be operably coupled to the sample substrate 108. The illustrated sample substrate 108 may include a flexible planar surface and adhesive associated with the flexible planar surface. In examples utilizing a flexible planar surface, the sample substrate 108 may be composed of an elastomeric material or the like. For example, the sample substrate 108 may be composed of an elastomeric material such as polydimethylsiloxane (PDMS) or the like.

As discussed above, contact device 106 may be adapted to contact a portion of a sample substrate 108 to one or more target substances 205 from a target substrate 110 at a given physical location. For example, contact device 106 may include one or more hydraulic devices, cams, rotational motors, linear actuators, biasing devices, the like, and/or combinations thereof configured to removably contact sample substrate 108 to target substrate 110.

The illustrated sample substrate 108 may include two or more portions, such as first portion 202 and second portion 204. In some examples, the first portion 202 of sample substrate 108 may be contacted to one or more target substances 205 from a first physical location 206. Similarly, the second portion 204 of sample substrate 108 may be contacted to one or more target substances 205 from a second physical location 208 of target substrate 110.

In some examples, contact device 106 may be adapted to contact a first portion 202 of sample substrate 108 to the target substrate 110 while simultaneously restraining a second portion 202 of sample substrate 108 from contact with the target substrate 110. In examples where the sample substrate 108 may be composed of an elastomeric material, contact device 106 may include a mechanical probe (not shown) adapted to press a first portion 202 of sample substrate 108 into contact with the target substrate 110 while simultaneously restraining other portions of sample substrate 108 from contact with the target substrate 110.

Figure 4:
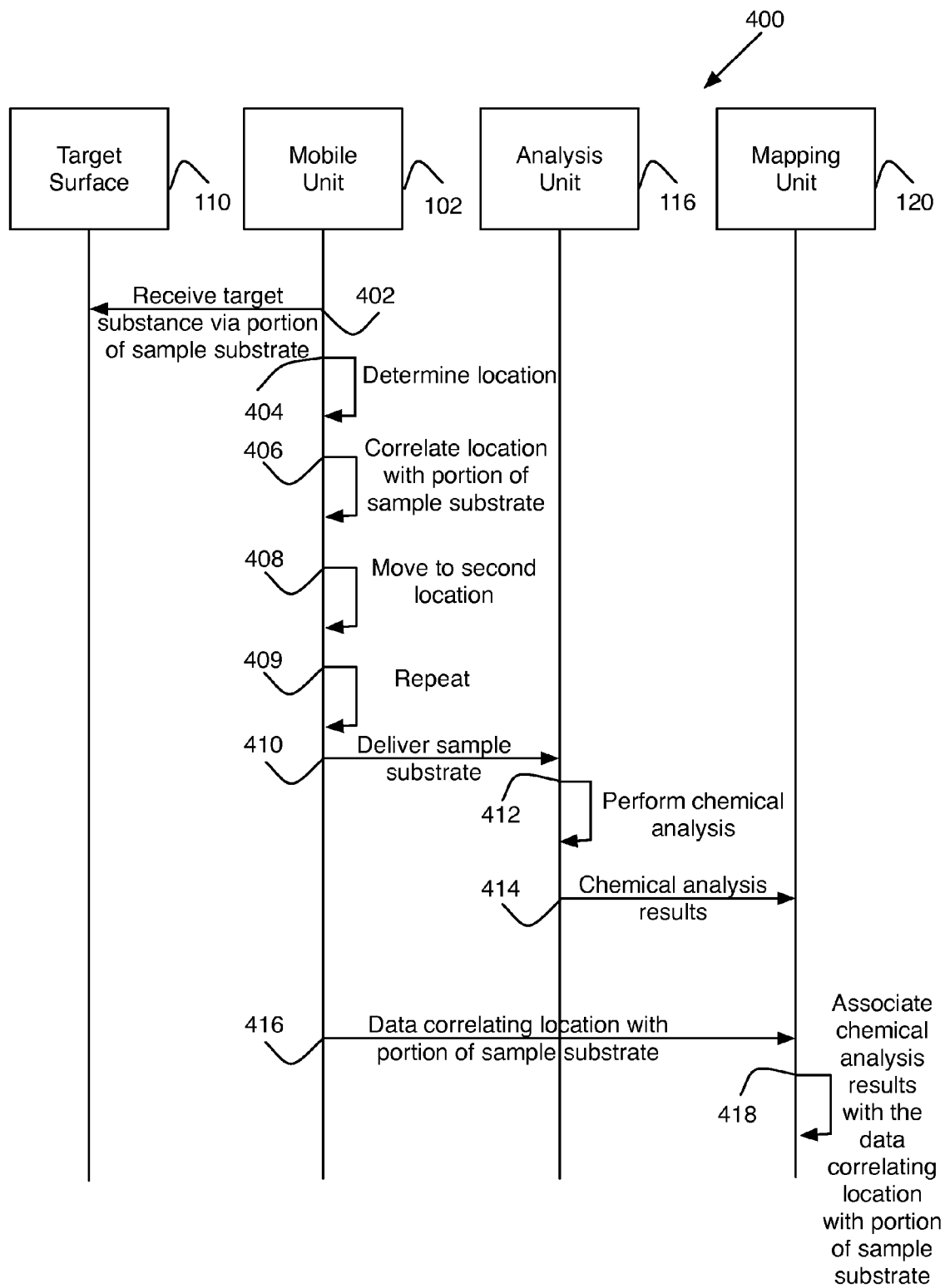
FIG. 4 illustrates an example process for mobile sampling of one or more target substances.

FIG. 4 illustrates an example process 400 for mobile sampling of one or more target substances, in accordance with at least some embodiments of the present disclosure. Process 400, and other processes described herein, set forth various functional blocks or actions that may be described as processing steps, functional operations, events and/or acts, etc., which may be performed by hardware, software, and/or firmware. Those skilled in the art in light of the present disclosure will recognize that numerous alternatives to the functional blocks shown in FIG. 4 may be practiced in various implementations. For example, although process 400, as shown in FIG. 4, comprises one particular order of blocks or actions, the order in which these blocks or actions are presented does not necessarily limit claimed subject matter to any particular order. Likewise, intervening actions not shown in FIG. 4 and/or additional actions not shown in FIG. 4 may be employed and/or some of the actions shown in FIG. 4 may be eliminated, without departing from the scope of claimed subject matter. Process 400 may include one or more of operations 402, 404, 406, 408, 409, 410, 412, 414, 416 and/or 418.

As illustrated, process 400 may be implemented for mobile sampling of one or more target substances via a mobile unit 102. At operation 402, one or more target substances associated with target surface 110 may be received from a first physical location 206 (FIG. 3) via a first portion 202 (FIG. 3) of a sample substrate 108 (FIG. 3). For example, one or more target substances may be transferred from a first physical location 206 (FIG. 3) to a first portion 202 (FIG. 3) of a sample substrate 108 (FIG. 3) via contact device 106 (FIG. 1) of mobile unit 102.

At operation 404, the first physical location 206 (FIG. 3) may be determined. For example, the first physical location 206 (FIG. 3) may be determined via location device 104 (FIG. 1) of mobile unit 102.

At operation 406, the first physical location 206 (FIG. 3) may be correlated with the first portion 202 (FIG. 3) of the sample substrate 108 (FIG. 3). For example, the first physical location 206 (FIG. 3) may be correlated with the first portion 202 (FIG. 3) of the sample substrate 108 (FIG. 3) via computing device 114 (FIG. 1) of mobile unit 102.

At operation 408, mobile unit 102 may be moved from the first physical location 206 (FIG. 3) to a second physical location 208 (FIG. 3). For example, mobile unit 102 may be moved from the first physical location 206 (FIG. 3) to a second physical location 208 (FIG. 3) via locomotion device 112 (FIG. 1) of mobile unit 102.

At operation 409, one or more of operations 402-408 may be repeated. In one example, one or more target substances may be received from a second physical location 208 (FIG. 3) via a second portion 204 (FIG. 3) of a sample substrate 108 (FIG. 3) via contact device 106 (FIG. 1) of mobile unit 102. Similarly, the second physical location 208 (FIG. 3) may be determined via location device 104 (FIG. 1) of mobile unit 102. Likewise, the second physical location 208 (FIG. 3) may be correlated with the second portion 204 (FIG. 3) of the sample substrate 108 (FIG. 3) via computing device 114 (FIG. 1) of mobile unit 102. In some examples, the first physical location 206 (FIG. 3) and the second physical location 208 (FIG. 3) may be associated with a target substrate 110. In other examples, the first physical location 206 (FIG. 3) may be associated with a first target substrate 110 and the second physical location 208 (FIG. 3) may be associated with a second target substrate (not shown).

At operation 410, the sample substrate 108 (FIG. 3) may be delivered from the mobile unit 108 to an analysis unit 116 capable of performing a chemical analysis. Alternatively, in some examples the mobile unit 102 may be operably coupled to the analysis unit 116 and adapted to move the analysis unit 116 between physical locations. In such a case, the mobile unit 102 may move the analysis unit 114 from location to location so that the analysis unit 114 may perform a chemical analysis as the end of gathering target substances onto the sample substrate 108 (FIG. 3). Alternatively, the mobile unit 102 may move the analysis unit 114 from location to location so that the analysis unit 114 may perform a chemical analysis at designated intervals.

At operation 412, a chemical analysis may be performed on the first portion 202 (FIG. 3) of the sample substrate 108 (FIG. 3) and the second portion 204 (FIG. 3) of the sample substrate 108 (FIG. 3). For example, a chemical analysis may be performed on the first portion 202 (FIG. 3) of the sample substrate 108 (FIG. 3) and the second portion 204 (FIG. 3) of the sample substrate 108 (FIG. 3) via analysis unit 116.

At operation 414, chemical analysis result may be communicated to mapping unit 120 from analysis unit 116. At block 416, data correlating physical locations with portions 202/204 (FIG. 3) of the sample substrate 108 (FIG. 3) may be communicated to mapping unit 120 from mobile unit 102. It should be noted that in some examples two or more of mobile unit 102, analysis unit 116, and/or mapping unit 120 may share common computing device(s) 114 (FIG. 1), potentially simplifying or eliminating blocks 414 or 416.

At operation 418, a chemical analysis result of the first portion 202 (FIG. 3) of the sample substrate 108 (FIG. 3) and a chemical analysis result of the second portion 204 (FIG. 3) of the sample substrate 108 (FIG. 3) may be associated with a geometric map. For example, based at least in part on the correlation of the first physical location 206 (FIG. 3) and the second physical location 208 (FIG. 3) with the first portion 202 (FIG. 3) of the sample substrate 108 (FIG. 3) and the second portion 204 (FIG. 3) of the sample substrate 108 (FIG. 3), mapping unit 120 may associate such chemical analysis results with a geometric map. Such a geometric map may be representative of at least a portion of target surface 110.

Figure 5:
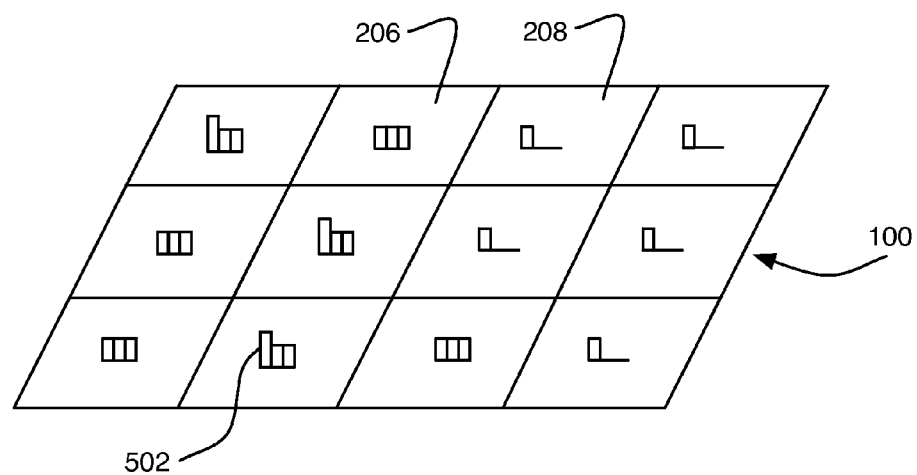
FIG. 5 illustrates an example geometric map with associated chemical analysis results.

FIG. 5 illustrates an example geometric map 500 with associated chemical analysis results, in accordance with at least some embodiments of the present disclosure. In the illustrated example, a geometric map 500 may be representative of at least a portion of target surface 110. For example, geometric map 500 may be representative of two or more physical location sampled by mobile unit 102 (FIG. 3), such as the first physical location 206 and the second physical location 208. Additionally, chemical analysis results 502 may be associated with two or more physical location sampled by mobile unit 102 (FIG. 3).

Accordingly, geometric map 500 may overlay chemical analysis results 502 with physical location data sampled by mobile unit 102 (FIG. 3). Such a geometric map 500 overlaid with chemical analysis results 502 may visually indicate the existence and/or pattern of wanted or unwanted target substance across a geometric space.

In some cases, such mobile sampling may be utilized by industrial or medical users to identify the physical location and/or distribution of one or more target compounds of interest across a geometric space. For example, such industrial or medical users may include petrochemical facilities, hospitals, food service facilities, the like, and/or combinations thereof.

In a chemical industry example, an area of a chemical spill that is otherwise invisible to the eye may be subject to mobile sampling of one or more target substances and a geometric map 500 may be overlaid with chemical analysis results 502 that may visually indicate the existence and/or pattern of such a chemical spill across a geometric space. In a food service industry example, mobile sampling of one or more target substances may be utilized to scan a floor of a food handling facility for molecules specific to a rodent, and a geometric map 500 may be overlaid with chemical analysis results 502 that may visually indicate the a rodent point of entry across a geometric space. In a medical facility example, an autonomously mobile sampling of one or more target substances may be utilized to scan the floors for chemical evidence left by pathogens, and thereby alert the medical staff to potential care issues.

FIG. 6 illustrates an example computer program product 600 that is arranged in accordance with the present disclosure. Program product 600 may include a signal bearing medium 602. Signal bearing medium 602 may include one or more machine-readable instructions 604, which, if executed by one or more processors, may operatively enable a computing device to provide the functionality described above with respect to FIG. 4. Thus, for example, referring to the system of FIG. 1, system 100, mobile unit 102, analysis unit 116, and/or mapping unit 120 may undertake one or more of the actions shown in FIG. 4 in response to instructions 604 conveyed by medium 602.

In some implementations, signal bearing medium 602 may encompass a computer-readable medium 606, such as, but not limited to, a hard disk drive, a Compact Disc (CD), a Digital Video Disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.).

Figure 7:
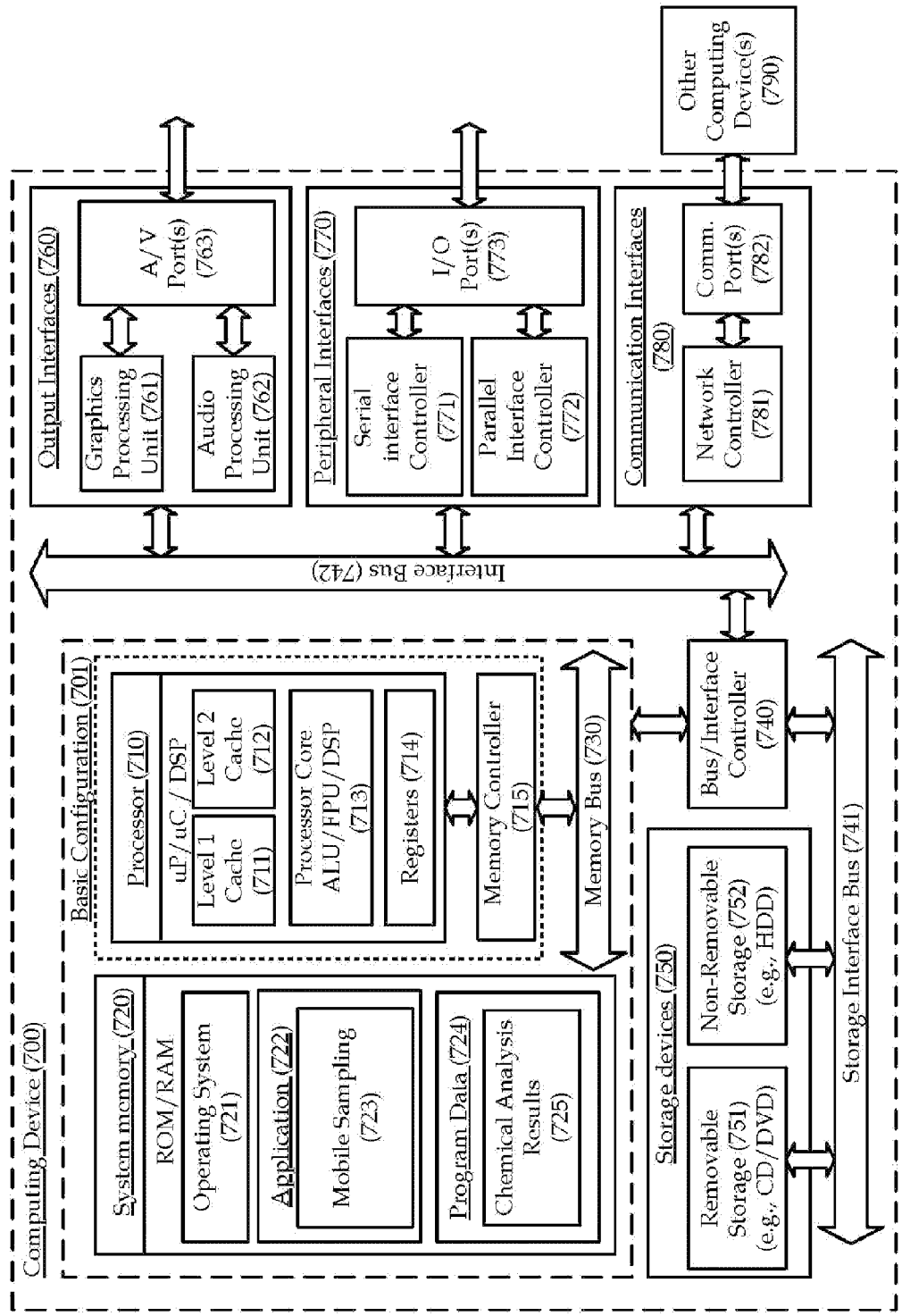
FIG. 7 is a block diagram illustrating an example computing device, all arranged in accordance with the present disclosure.

FIG. 7 is a block diagram illustrating an example computing device 700 that is arranged in accordance with the present disclosure. In one example configuration 701, computing device 700 may include one or more processors 710 and system memory 720. A memory bus 730 can be used for communicating between the processor 710 and the system memory 720.

Depending on the desired configuration, processor 710 may be of any type including but not limited to a microprocessor (μP), a microcontroller (μC), a digital signal processor (DSP), or any combination thereof. Processor 710 can include one or more levels of caching, such as a level one cache 711 and a level two cache 712, a processor core 713, and registers 714. The processor core 713 can include an arithmetic logic unit (ALU), a floating point unit (FPU), a digital signal processing core (DSP Core), or any combination thereof. A memory controller 715 can also be used with the processor 710, or in some implementations the memory controller 715 can be an internal part of the processor 710.

Depending on the desired configuration, the system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include a mobile sampling algorithm 723 in a mobile unit, analysis unit, and/or a mapping unit 120 that is arranged to perform the functions and/or operations as described herein including the functional blocks and/or operations described with respect to process 400 of FIG. 4. Program Data 724 may include data 725 for use in mobile sampling algorithm 723, for example, data corresponding to chemical analysis results and/or data correlating physical locations with portions of a sample substrate. In some example embodiments, application 722 may be arranged to operate with program data 724 on an operating system 721 such that implementations of mobile sampling may be provided as described herein. This described basic configuration is illustrated in FIG. 7 by those components within dashed line 701.

Computing device 700 may have additional features or functionality, and additional interfaces to facilitate communications between the basic configuration 701 and any required devices and interfaces. For example, a bus/interface controller 740 may be used to facilitate communications between the basic configuration 701 and one or more data storage devices 750 via a storage interface bus 741. The data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of device 700.

Computing device 700 may also include an interface bus 742 for facilitating communication from various interface devices (e.g., output interfaces, peripheral interfaces, and communication interfaces) to the basic configuration 701 via the bus/interface controller 740. Example output interfaces 760 may include a graphics processing unit 761 and an audio processing unit 762, which may be configured to communicate to various external devices such as a display or speakers via one or more A/V ports 763. Example peripheral interfaces 760 may include a serial interface controller 771 or a parallel interface controller 772, which may be configured to communicate with external devices such as input devices (e.g., keyboard, mouse, pen, voice input device, touch input device, etc.) or other peripheral devices (e.g., printer, scanner, etc.) via one or more I/O ports 773. An example communication interface 780 includes a network controller 781, which may be arranged to facilitate communications with one or more other computing devices 790 over a network communication via one or more communication ports 782. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 700 may also be implemented as a personal computer including both laptop computer and non-laptop computer configurations. In addition, computing device 700 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A system arranged to sample one or more target substances, the system comprising:
 a mobile unit comprising: a location device adapted to determine a first physical location of the mobile unit; a contact device operably coupled to a sample substrate, wherein the sample substrate comprises a flexible tape including at least polyethylene terephthalate ($C_{10}H_8O_4$) and adhesive associated with the flexible tape and the contact device being adapted to contact a first portion of the sample substrate to a number of target substances from the first physical location; a computing device adapted to correlate the first physical location of the mobile unit with the first portion of the sample substrate; and a locomotion device adapted to move the mobile unit from the first physical location to a second physical location;

an analysis unit comprising a chemical analysis device adapted to perform a chemical analysis of two or more portions of the sample substrate to provide a chemical analysis result; and a mapping unit configured to communicate with the analysis unit and the mobile unit, wherein the mapping unit is adapted to associate the chemical analysis result of the two or more portions of the sample substrate with a geometric map of the first physical location and the second physical location.

2. The system of claim 1, wherein the mobile unit is operably coupled to the analysis unit and adapted to move the analysis unit from the first physical location to the second physical location.

3. The system of claim 1, wherein the mobile unit is operably coupled to the analysis unit and the mapping unit, and wherein the mobile unit is adapted to move the analysis unit and the mapping unit from the first physical location to the second physical location.

4. The system of claim 1, wherein the mobile unit, analysis unit, and the mapping unit share the computing device.

5. The system of claim 1, wherein the mobile unit and the analysis unit are adapted to move independently from each other.

6. A mobile unit arranged to sample one or more target substances, the mobile unit comprising:

a location device adapted to determine a first physical location of the mobile unit;

a contact device operably coupled to a sample substrate, wherein the sample substrate comprises a flexible tape including at least polyethylene terephthalate ($C_{10}H_8O_4$) and adhesive associated with the flexible tape and the contact device being adapted to contact a first portion of the sample substrate to a number of target substances from the first physical location;

a computing device adapted to correlate the first physical location of the mobile unit with the first portion of the sample substrate; and a locomotion device adapted to move the mobile unit from the first physical location to a second physical location.

7. The mobile unit of claim 6, further comprising a mapping unit operably coupled to the locomotion device, the mapping unit adapted to associate a chemical analysis result of the two or more portions of the sample substrate with a geometric map of the first physical location and the second physical location.

8. The mobile unit of claim 6, further comprising:

an analysis unit operably coupled to the locomotion device, the analysis unit comprising a chemical analysis device adapted to perform a chemical analysis of two or more portions of the sample substrate; and a mapping unit operably coupled to the locomotion device, the mapping unit adapted to associate a chemical analysis result of the two or more portions of the sample substrate with a geometric map of the first physical location and the second physical location.

9. The mobile unit of claim 6, further comprising an analysis unit operably coupled to the locomotion device, the analysis unit comprising a chemical analysis device adapted to perform a chemical analysis of two or more portions of the sample substrate, wherein the mobile unit and the analysis unit are adapted to move independently from each other.

* * * * *

UNITED STATES PATENT AND TRADEMARK OFFICE
CERTIFICATE OF CORRECTION

| | | |
|---|---|---|
| PATENT NO. | : 8,407,011 B2 | Page 1 of 2 |
| APPLICATION NO. | : 12/534393 | |
| DATED | : March 26, 2013 | |
| INVENTOR(S) | : Miller | |

It is certified that error appears in the above-identified patent and that said Letters Patent is hereby corrected as shown below:

On the Title Page, Item (56), under "OTHER PUBLICATIONS", in Column 2, Line 7, delete "al," and insert -- al., --, therefor.

On the Title Page, Item (56), under "OTHER PUBLICATIONS", in Column 2, Line 13, delete "al," and insert -- al., --, therefor.

In the Drawings:

In Fig. 5, Sheet 4 of 6, insert main designator - - 500 - -, above the figure.

In Fig. 5, Sheet 4 of 6, delete Tag "100" and insert - - 110 - -, therefor.

In Fig. 7, Sheet 6 of 6, delete "uP / uC / DSP" and insert - - μP/μC/DSP - -, therefor.

In the Specification:

In Column 3, Line 13, delete "112." and insert - - 110. - -, therefor.

In Column 3, Line 63, delete "analysis unit 114 or" and insert - - analysis unit 116 or - -, therefor.

In Column 3, Lines 63-64, delete "analysis unit 114 from" and insert - - analysis unit 116 from - -, therefor.

In Column 3, Lines 66-67, delete "analysis unit 114" and insert - - analysis unit 116 - -, therefor.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,407,011 B2

In Column 3, Lines 5-6, delete "analysis unit 114" and insert -- analysis unit 116 --, therefor.

In Column 3, Line 8, delete "analysis unit 114" and insert -- analysis unit 116 --, therefor.

In Column 3, Line 9, delete "analysis unit 114" and insert -- analysis unit 116 --, therefor.

In Column 4, Line 5, delete "analysis unit 114" and insert -- analysis unit 116 --, therefor.

In Column 6, Line 12, delete "202" and insert -- 204 --, therefor.

In Column 7, Line 17, delete "108" and insert -- 102 --, therefor.

In Column 7, Line 22, delete "analysis unit 114" and insert -- analysis unit 116 --, therefor.

In Column 7, Line 23, delete "analysis unit 114" and insert -- analysis unit 116 --, therefor.

In Column 7, Line 26, delete "analysis unit 114" and insert -- analysis unit 116 --, therefor.

In Column 7, Line 27, delete "analysis unit 114" and insert -- analysis unit 116 --, therefor.

In Column 9, Line 37, delete "(HDD)," and insert -- (HDDs), --, therefor.

In Column 9, Line 39, delete "(SSD)," and insert -- (SSDs), --, therefor.

In Column 9, Line 49, delete "(DVD)" and insert -- (DVDs) --, therefor.

In Column 9, Line 64, delete "760" and insert -- 770 --, therefor.